(12) United States Patent
Sánchez-Ferrer et al.

(10) Patent No.: US 6,730,497 B2
(45) Date of Patent: May 4, 2004

(54) PROCESS FOR PREPARING CEPHALOSPORANIC ACID DERIVATIVES USING β-KETOACID DERIVATIVES

(75) Inventors: Alvaro Sánchez-Ferrer, Murcia (ES); José Aniceto López-Más, Alicante (ES); Francisco García-Carmona, Murcia (ES)

(73) Assignee: Bioferma Murcia S.A., Murcia (ES)

( * ) Notice: Subject to any disclaimer, the term of this patent is extended or adjusted under 35 U.S.C. 154(b) by 0 days.

(21) Appl. No.: 10/125,458

(22) Filed: Apr. 19, 2002

(65) Prior Publication Data

US 2003/0104515 A1 Jun. 5, 2003

(30) Foreign Application Priority Data

| Apr. 19, 2001 | (EP) | 01201426 |
| May 9, 2001 | (EP) | 01201699 |
| May 9, 2001 | (EP) | 01201718 |
| Nov. 30, 2001 | (IE) | 2001/1025 |
| Nov. 30, 2001 | (IE) | 2001/1024 |

(51) Int. Cl.[7] .................................................. C12P 35/00
(52) U.S. Cl. .......................... 435/47; 540/224; 540/229
(58) Field of Search ............................... 540/224, 229; 435/47

(56) References Cited

U.S. PATENT DOCUMENTS

| 3,278,531 A | 10/1966 | Cox et al. | 260/243 |
| 3,367,933 A | 2/1968 | Eardley et al. | 260/243 |
| 3,872,115 A | 3/1975 | Sugimoto et al. | 260/243 |
| 3,960,662 A | 6/1976 | Matsuda et al. | 195/29 |
| 4,745,061 A | 5/1988 | Aretz et al. | 435/193 |
| 4,774,179 A | 9/1988 | Ichikawa et al. | 435/51 |
| 5,296,358 A | 3/1994 | Battistel et al. | 435/49 |

FOREIGN PATENT DOCUMENTS

| CH | 520709 | 5/1972 |
| DE | 1953861 | 5/1971 |
| EP | 0315786 A1 | 5/1989 |
| EP | 0167651 B1 | 9/1989 |
| EP | 0283218 B1 | 7/1993 |
| EP | 036427 B1 | 5/1995 |
| EP | 0496993 B1 | 8/1996 |
| EP | 0517200 B1 | 8/1996 |
| EP | 0846695 A1 | 6/1998 |
| FR | 2241557 | 3/1975 |
| GB | 1239814 | 7/1971 |
| GB | 1272769 | 5/1972 |
| GB | 1295841 | 11/1972 |
| GB | 1385685 | 2/1975 |
| JP | 56-164194 | 12/1981 |
| JP | 59-170095 | 9/1984 |
| JP | 2-270883 | 11/1990 |
| WO | WO90/12110 | 10/1990 |
| WO | WO95/12680 | 5/1995 |
| WO | WO95/35020 | 12/1995 |
| WO | WO96/16174 | 5/1996 |

OTHER PUBLICATIONS

Pszczola, Food Technology, vol. 52, No. 3, Mar. 1998, pp. 30–35, The AB s of Nutraceutical Ingredients.

Schaefer et al, Kidney Intl, vol. 36, Supp. 27, 1989, pp. S136–S139, Calcium salts of ketoacids as a new treatment strategy . . .

Buto et al, Biotechnology & Bioengineering, vol. 44, 1994, pp. 1288–1294, Evaluation of D–Amino Acid Oxidase from . . .

Savidge, Biotechnology of Industrial Antibiotics, Chapter 5, 1984, Enzymatic Conversions Used in the Biotechnology, 18 (1), 1998, pp. 1–12, Recent Trends in Enzymatic Conversion of Used in the Production of . . .

Parmar et al, Critical Reviews in Biotechnology, 18 (1), 1998, pp. 1–12, Recent Trends in Enzymatic Conversion of . .

Conlon et al, Biotechnology & Bioengineering, vol. 46, 1995, pp. 510–513, Two–Step Immobilized Enzyme Conversion of . . .

Won et al, Applied Biochemistry and Biotechnology, vol. 69, 1998 pp. 1–9, The Effect of 2–Mercapto–5–Methyl–1, 3,4–. . .

(List continued on next page.)

Primary Examiner—Herbert J. Lilling
(74) Attorney, Agent, or Firm—Jacobson Holman PLLC

(57) ABSTRACT

A process for preparing cephalosporanic acid derivatives comprises the steps of enzymatically converting a 3-thiolated cephalosporin C compound of formula III:

(III)

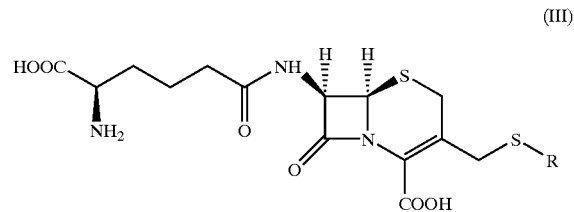

into a 3-thiolated-α-ketoadipyl-7-aminocephalosporanic acid derivative of formula IV:

(IV)

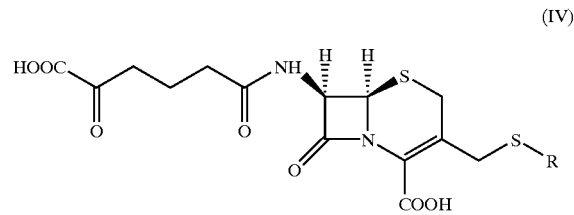

wherein R is a heterocyclic group comprising at least a nitrogen atom.

Compounds of formula IV are used in the preparation of cephalosporin C antibiotics and derivatives thereof.

15 Claims, No Drawings

OTHER PUBLICATIONS

Riethorst et al, Chimia 53, 1999, pp. 600–607, An Industrial View on Enzymes for the Cleavage of Cephalosporin C.

Kubicek–Pranz et al, Jour of Applied Biochemsitry 7, 1985, pp. 104–113, D–Amino Acid Oxidase from the Yeast Trigonopsis . . .

Szwajcer et al, Biotechnology Ltrs., vol. 7, No. 1, 1985, pp. 1–7, Isolation and Partial Characterization of a D–Amino Acid . . .

Kramer et al, Tetrahedron, 53 (43), 1997, pp. 14645–14650, Coimmobilization of L–α–Glycerophosphate Oxidase with . . .

Hannah et al, Jour of Medicinal Chemistry, vol. 25, No. 4, 1982, pp. 457–469, Quaternary Heterocyclylamino β–Lactams: A . . .

Nomura et al, Jour of Medicinal Chemistry, vol. 17, No. 12, 1974 Semisynthetic β–Lactam Antibiotics 6. Sulfocephalosporins and . . .

Cocker et al, Jour of Chemical Society, 1965, pp. 5015–5031, Cephalosporanic Acids. Part II. Displacement of the . . .

Justiz et al, Jour Organic Chemistry 62, 1997, pp. 9099–9106, One–Pot Chemoenzymatic Synthesis of 3'–Functionalized . . .

The Merck Index on CD–ROM, Version 12:2, 1997, Merck & Co., Inc., XP002177921, 4 pgs.

PROCESS FOR PREPARING CEPHALOSPORANIC ACID DERIVATIVES USING β-KETOACID DERIVATIVES

INTRODUCTION

The invention relates to a process for preparing 3-cephalosporin C derivatives which are used in the preparation of β-lactam antibiotics. In particular the invention relates to an enzymatic process for the preparation acid (3-thiolated-7-ACA) using α-ketoacid intermediates. The α-ketoacids or α-oxoacids are important biopharmaceutical compounds.

Oxoacids of essential amino acids are gaining importance as nutraceuticals (Pszcola, D E, *Food Technol.* 52, 30, 1998) as well as therapeutic agents for treating nitrogen accumulation disorders (Schaefer et al., *Kidney Int. Suppl.* 27, S136, 1989; Buto et al, *Biotechnol. Bioeng.* 44, 1288, 1994). Another important application is the production of 7-amino cephalosporanic acid (Savidge, T A; In *Biotechnology of Industrial Antibiotics*, p 171, Marcel Dekker, New York, 1984) from cephalosporin C (3-acetoxymethyl-7β-(D-5-amino-5-carboxypentanamido) ceph-3-em-4-carboxylic acid). The transformation can be carried out by a D-amino acid transaminase from *Bacillus licheniformis* ATCC 9945, which converts cephalosporin C with α-ketoacids into α-ketoadipyl-7-ACA and the corresponding D-α-amino acid, as described in DE 3447023 (Hoechst). This conversion is a transamination, the amino group of cephalosporin C being converted non-oxidatively into the keto group, without the release of hydrogen peroxide. However there is a low level of activity of this enzyme, as described in EP 0315786.

Chemical methods for the preparation of 3-thiolated-7-ACA cephalosporanic acid derivatives are known (U.S. Pat. No. 3,367,933; BE 718,824), however they have disadvantages such as low temperature reaction conditions, the use of costly and toxic solvents or reagents and chemical instability of intermediates which makes the processes difficult on an industrial scale.

To overcome the drawbacks of the chemical route to 7-ACA, alternative enzymatic cleavage of cephalosporin C has been described. Direct one-step removal of the lateral 7'-aminoadipic side-chain of cephalosporin C is possible by using specific cephalosporin acylases (FR 2,241,557; U.S. Pat. No. 4,774,179; EP 283,248; WO 9512680; WO 9616174). These processes, however, are often not reproducible and are characterised by low yields and lengthy reaction times as described in U.S. Pat. No. 5,296,358. No industrial application of this technology (single-step conversion of cephalosporin C to 7-ACA) has been reported at this time (Parmar et al, Crit. Rev. Biotechnol. 18, 1, 1998).

On the other hand, processes that transform the cephalosporin C into 7-ACA by means of two enzymatic steps are important from an industrial point of view. The first stage consists of using a D-amino acid oxidase (E.C. 1.4.3.3, hereinbelow indicated as DAAO) from different sources (*Trigonopsis variabilis*, GB 1,272,769; *Rhodotorula gracilis*, EP 0,517,200; or *Fusarium solari M*-0718, EP 0,364,275). DAAO oxidises the lateral D-5-amido-carboxypentanoyl chain of cephalosporin C in the presence of molecular oxygen, to produce 7β-(5-carboxy-5-oxopentamido)-ceph-3-em-carboxylic acid (or α-ketoadipyl-7-aminocephalosporanic acid, hereinbelow indicated as α-ketoadipyl-7-ACA) and hydrogen peroxide, which chemically decarboxylate the α-ketoadipyl-7-ACA to 7β-(4-carboxy butanamido)-ceph-3-em-4-carboxylic acid (or glutaryl-7-aminocephalo-sporanic acid, hereinbelow indicated as GL-7-ACA).

In a second stage, a specific acylase for GL-7-ACA, glutaryl-7-ACA acylase (E.C. 3.5.1.3), is used, for example that of a Pseudomonas type microorganism (U.S. Pat. No. 3,960,662, EP 0496993) over expressed in *E. coli*, which deacylates the GL-7-ACA into 7-amino-ceph-3-em4-carboxylic acid (or 7-amino cephalosporanic acid, hereinbelow indicated as 7-ACA).

This two-step enzymatic process for obtaining 7-ACA has been used on an industrial scale (Conlon et al. Biotechnol. Bioeng. 46, 510,1995).

Yet another advance in enzymatic processes, is disclosed in EP 0846695, in which solid glutaryl-7-ACA is reacted with a heterocyclic group that contains at least a nitrogen with or without a sulphur or oxygen atom to produce a 3-modified glutaryl-7-ACA. These 3-derivatives are enzymatically transformed to their corresponding 3-heterocyclic thiomethyl-7-ACA derivatives.

This procedure can be defined as an enzymatic-chemical-enzymatic (ECE) process, since the isolated GL-7-ACA comes from a bioconversion of solubilised cephalosporin C, then GL-7-ACA is reacted with the heterocyclic thiols and finally the 3-heterocyclic thio-derivative is enzymated with GL-7-ACA acylase. The problem with this method is the need to isolate GL-7-ACA, which given its high water solubility, is technically difficult and expensive, as described in WO 9535020.

An additional problem is that the enzyme can only be reused a few times due to the "poisoning" of the biocatalyst by the residual heterocyclic thiols. This poisoning effect is well documented with one of the thiols used, 5-methyl-1,3,4-thiadiazole-2-thiol (MMTD) (Won et al, App. Biochem. Biotech. 69, 1, 1998).

The oxidative deamination of the D-adipamido side chain of cephalosporin C under aerobic conditions into α-ketoadipyl-7-ACA has been described using D-amino acid oxidase (D-AAO) from cell-free extracts (GB 1,2 72,769, Glaxo) or in toluene-activated (permeabilised) cells (GB 1,385,685) of the yeast *Trigonopsis variabilis* or *Rhodotorula glutinis* (EP 0517200). In this reaction, molecular oxygen acts as the electron acceptor and is converted to hydrogen peroxide, which chemically reacts with the α-ketoadipyl-7-ACA producing its decarboxylation into glutaryl-7-ACA. In the presence of large quantities of the catalase produced for the above yeasts, the hydrogen peroxide is cleaved to water and molecular oxygen, rendering a mixture of α-ketoadipyl-7-ACA and glutaryl-7-ACA. The α-ketoadipyl-7-ACA is quite unstable (GB 1,385,685) and rapidly decomposes to unknown products and hence reduces the yield of glutaryl-7-ACA from 90 to 95% to 60 to 70%, depending on the yeast and strain (Parmar et al, *Crit. Rev. Biotechnol.* 18, 1, 1998; Rietharst, W. and Riechert, A, *Chimia* 53, 600, 1999). As a result no industrial application has been described.

There is therefore a need for an efficient and improved process for the preparation of 3-thiolated-7-ACA cephalosporanic acid derivatives on an industrial scale. In addition the isolation of stable α-ketoacid derivatives which are important biopharmaceutical compounds would be beneficial.

STATEMENTS OF INVENTION

According to the invention there is provided a process for preparing cephalosporanic acid derivatives comprising the steps of:

enzymatically converting a 3-thiolated cephalosporin C compound of formula III:

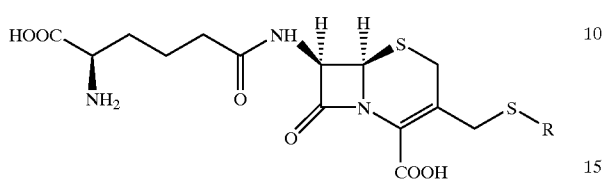

(III)

into a 3-thiolated-α-ketoadipyl-7-aminocephalosporanic acid derivative of formula IV:

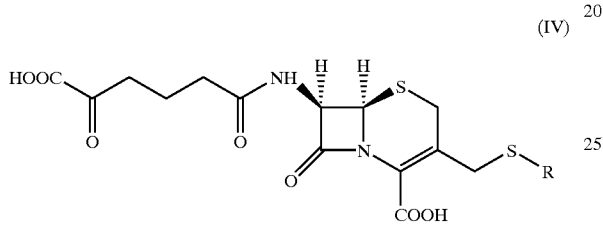

(IV)

wherein R is a heterocyclic group comprising at least a nitrogen atom.

Preferably the compound of formula III is enzymatically converted into a compound of formula IV by an immobilised enzyme system. Most preferably the enzyme system comprises co-immobilised D-Amino acid oxidase and catalase. Preferably the enzymatic conversion is carried out in the presence of molecular oxygen, at a pressure of 1 to 5 bar absolute, a pH of from 6.5 to 8.0 and at a temperature of from 15 to 30° C. for a period of from 30 mins to 180 mins.

Preferably the process comprises the step of separating the enzyme system from the reaction mixture, preferably by filtration.

In one embodiment of the invention the process includes the step of purifying the compound of formula IV.

Most preferably the compound is purified using an adsorption column. Preferably the enzymes are co-immobilised using a suitable cross-linker agent in a suitable solid support. The enzymes may be in the form of crystals of a size suitable for use as a biocatalyst.

Preferably the enzymatic processes are carried out while maintaining the enzyme in dispersion in an aqueous substrate solution. Preferably the or each enzymatic process is carried out in a column. Most preferably the process includes the step of recovering the enzyme for reuse.

In one embodiment of the invention the compound of formula IV is used without purification in a continuous process for obtaining any useful derivative.

Preferably the R group in compounds of formula III and IV is a heterocyclic group comprising at least one nitrogen atom and optionally a sulphur or oxygen atom.

Most preferably R is a heterocyclic group selected from any one or more of the group comprising thienyl, diazolyl, tetrazolyl, thiazolyl, triazinyl, oxazolyl, oxadiazolyl, pyridyl, pirimidinyl, benzo thiazolyl, benzimidazolyl, benzoxazolyl, or any derivative thereof, preferably 5-methyl-1,3,4-thiadiazol-2-yl, 1-methyl-1H-tetrazol-5-yl or 1,2,5,6-tetrahydro-2-methyl-5,6-dioxo-1,2,4-triazin-3-yl.

The invention provides a 3-thiolated-α-ketoadipyl-7-aminocephalosporanic acid derivative of formula IV whenever prepared by a process of the invention.

The invention provides a compound of the Formula:

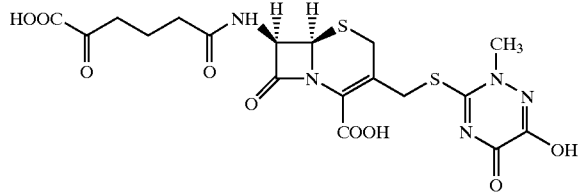

wherein in formula IV, R is 1,2,5,6-tetrahydro-2-methyl-5,6-dioxo-1,2,4-triazin-3-yl.

The invention provides a compound of the Formula:

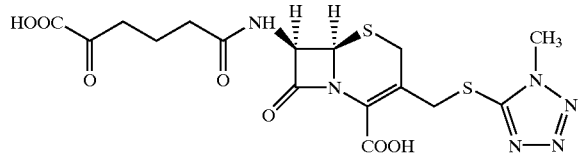

wherein in formula IV, R is 1-methyl-1H-tetrazol-5-yl.

The invention also provides use of a compound of formula IV as an intermediate in a process for preparing cephalosporin C antibiotics.

The invention also provides use of an intermediate compound of the formula:

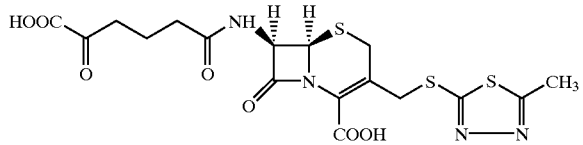

in a process for preparing cephalosporin C antibiotics wherein in formula IV R is 5-methyl-1,3,4-thiadiazol-2-yl.

The invention further provides a process for preparing cephalosporanic acid derivatives of the invention comprising the step of:

enzymatically converting a compound of formula IV to form a compound of formula I

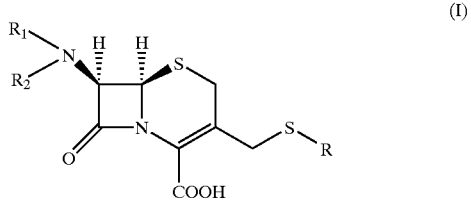

(I)

wherein R is a heterocyclic group comprising at least one nitrogen atom and $R_1$ and $R_2$ are both hydrogen atoms or one of them is a hydrogen atom and the other is an acyl donor.

Preferably the compound of formula IV is enzymatically converted to form a compound of formula I using Glutaryl-7-ACA acylase, most preferably the enzymation takes place at a temperature of approximately 20° C. and at a pH of between 6.5 and 8.0. Preferably the enzyme is immobilised using a suitable cross-linker agent in a suitable solid support.

Preferably the enzyme is in the form of crystals of a size suitable for use as a biocatalyst.

In one embodiment of the invention the enzymation is carried out while maintaining the enzyme in dispersion in an aqueous substrate solution. Preferably the enzymatic process is carried out in a column. Most preferably the process includes the step of recovering the enzyme for reuse.

The invention also provides use of a compound of formula I as an intermediate in a process for preparing cephalosporin C derivatives.

The invention further provides a process for preparing 3-thiolated cephalosporanic acid derivatives comprising the steps of;

enzymatically converting a compound of formula III

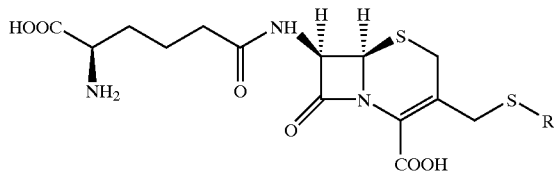

(III)

into a 3-thiolated-α-ketoadipyl-7-aminocephalosporanic acid derivative of formula IV:

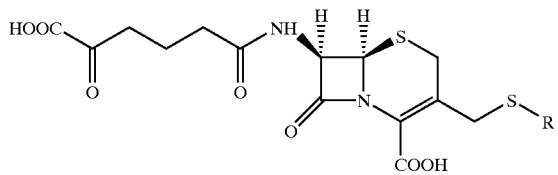

(IV)

and enzymatically converting a compound of formula IV to form a 3-thiolated 7-ACA compound of formula I

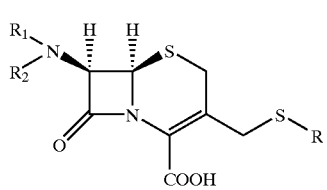

(I)

wherein R is a heterocyclic group comprising at least one nitrogen atom and $R_1$ and $R_2$ are both hydrogen atoms or one of them is a hydrogen atom and the other is an acyl donor.

In one embodiment of the invention the compound of formula III is enzymatically converted into a compound of formula I in one step by an immobilised enzyme system. Most preferably the enzyme system comprises a combination of co-immobilised D-amino acid oxidase/catalase in the presence of immobilised Glutaryl-7-ACA acylase. Preferably the enzymation takes place at a temperature of approximately 20° C. and at a pH of between 6.5 and 8.0. Most preferably the enzymes are co-immobilised using a suitable cross-linker agent in a suitable solid support.

Preferably the enzymes are in the form of crystals of a size suitable for use as a biocatalyst.

Most preferably the enzymatic processes are carried out while maintaining the enzyme in dispersion in an aqueous substrate solution.

Preferably the or each enzymatic process is carried out in a column. Most preferably the process includes the step of recovering the enzyme for reuse.

In one embodiment of the invention the compound of formula III is used without purification in a continuous process for obtaining any useful derivative.

The invention also provides a process for preparing cephalosporanic acid derivatives comprising the steps of:

reacting cephalosporin C with a thiol compound of the general formula II

R—SH                II wherein R is a heterocyclic group comprising at least one nitrogen atom, to form a 3-thiolated cephalosporin compound of formula III

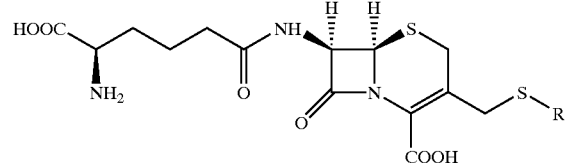

(III)

wherein R is as defined above, and, after formation of the compound of formula III removing excess thiol of formula II.

In one embodiment of the invention the excess thiol is removed by adsorption on an anion exchange resin. Preferably the anion exchange resin is a microporous resin having a cross-linked acrylic copolymer structure. Most preferably the anion exchange resin comprises an 8% cross-linking containing functional thialkyl benzyl ammonium group. The resin may be in the chloride, hydroxy, phosphate or acetate cycle.

In another embodiment of the invention the excess thiol is removed by crystallisation. Preferably crystallisation is carried out at an acidic pH.

In a further embodiment of the invention the excess thiol is removed by crystallisation followed by adsorption on an anion exchange resin.

Preferably the cephalosporin C is in an aqueous medium, Most preferably the cephalosporin C is in the form of a concentrated cephalosporin C solution.

Preferably the reaction is carried out at a pH of between 5.5 and 8.0, at a temperature of from 60° C. to 80° C., for a period of from 1 to 8 hours. Most preferably the reaction is carried out at a pH of approximately 6.0 and at a temperature of approximately 65° C.

In one embodiment of the invention the thiol compound is present in an amount of between 1 and 5 mol/mol of cephalosporin C.

Preferably R is a heterocyclic group comprising at least one nitrogen atom and optionally a sulphur or oxygen atom. Most preferably R is a heterocyclic group selected from any one or more of thienyl, diazolyl, thiazolyl, tetrazolyl, thiadiazolyl, triazinyl, oxazolyl, oxadiazolyl, pyridyl, pirimidinyl, benzothiazolyl, benzimidazolyl, benzoxazolyl, or any derivative thereof, preferably 5-methyl-1,3,4-thiadiazol-2-yl, 1-methyl-tetrazol-5-yl or 1,2,5,6-tetrahydro-2-methyl-5,6-dioxo-1,2,4-triazin-3-yl.

The invention provides a compound of formula III

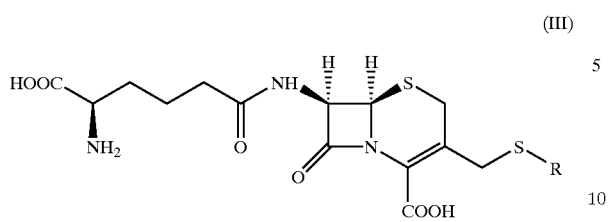
(III)

wherein R is a heterocyclic group comprising at least one nitrogen atom,

The invention provides a compound of the formula:

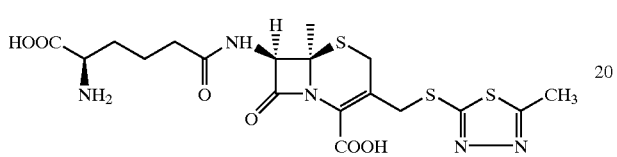

wherein in formula III R is 5-methyl-1,3,4-thiadiazol-2-yl.

The invention further provides a compound of the formula:

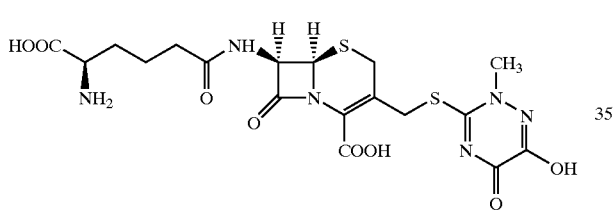

wherein the formula III R is 1,2,5,6-tetrahydro-2-methyl-5,6-dioxo-1,2,4-triazin-3-yl.

The invention also provides use of a compound of formula III as an intermediate in a process for preparing cephalosporin C derivatives.

One embodiment of the invention provides a process for preparing cephalosporanic acid derivatives comprising the steps of:

enzymatically converting a 3-thiolated cephalosporin C compound of formula III obtained by a process as described above:

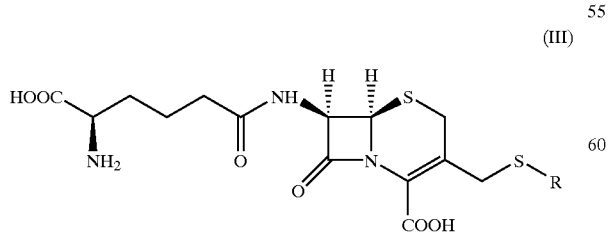
(III)

into a 3-thiolated-α-ketoadipyl-7-aminocephalosporanic acid derivative of formula IV:

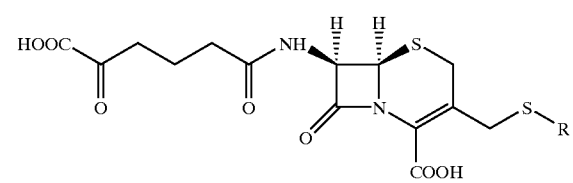
(IV)

wherein R is a heterocyclic group comprising at least a nitrogen atom.

In one embodiment of the invention the process additionally comprises the step of:

enzymatically converting a 3-thiolated α-ketoadipyl 7-ACA compound of formula IV

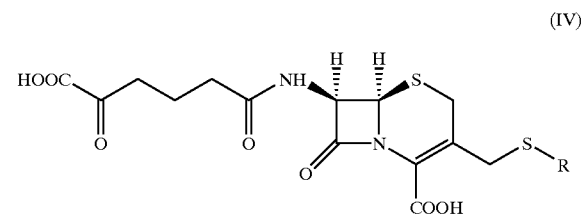
(IV)

to form a 3-thiolated 7-ACA compound of formula I

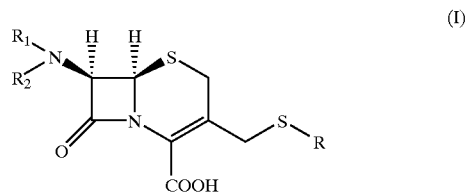
(I)

wherein R is a heterocyclic group comprising at least one nitrogen atom and $R_1$ and $R_2$ are both hydrogen atoms or one of them is a hydrogen atom and the other is an acyl donor.

Another embodiment of the invention provides a process for preparing cephalosporanic acid derivatives comprising the step of:

enzymatically converting a compound of formula IV

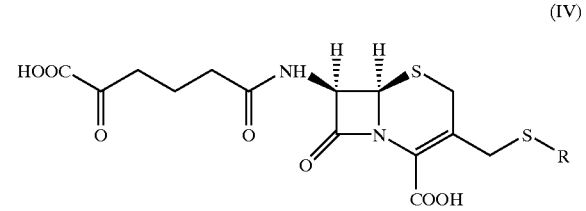
(IV)

to form a compound of formula I

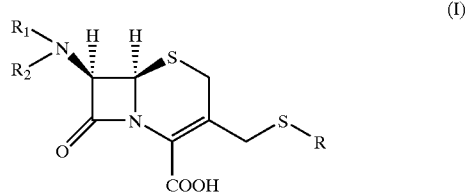
(I)

3-thiolated-7-ACA (T'X'A)

wherein R is a heterocyclic group comprising at least one nitrogen atom and $R_1$ and $R_2$ are both hydrogen atoms or one of them is a hydrogen atom and the other is an acyl donor.

Preferably a compound of formula IV is enzymatically converted to form a compound of formula I with Glutaryl-7-ACA acylase.

Most preferably compounds of formula I, III and IV are in a solid form or in the form of a non-toxic salt thereof.

The invention provides a process for the preparation of cephalosporin C antibiotics and derivatives thereof comprising forming a compound of formula III, IV and I as hereinbefore defined and subsequent enzymation of the compound.

The antibiotic may be any one or more of cefazolin, cefazedone, cefoperazone, cefamandol, cefatriazine, cefotiam and ceftriaxone.

DETAILED DESCRIPTION

We have found that 3-thiolated cephalosporanic C derivatives may be enzymated into α-ketoacid derivatives in the presence of a co-immobilised D-amino acid oxidase/catalase system. These α-ketoacid derivatives have been shown to be stable when isolated. A new improved process to obtain 3-thiolated-7-ACA derivatives, both in one step or in two consecutive enzymatic steps is thereby provided.

The present invention relates to an improved and more efficient process for preparing compounds of formula I from cephalosporin C.

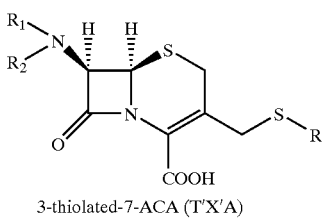

3-thiolated-7-ACA (T'X'A)

wherein R is a heterocyclic group comprising at least one nitrogen atom and $R_1$ and $R_2$ are both hydrogen atoms or one of them is a hydrogen atom and the other is an acyl donor.

The process involves the formation of new stable α-ketoadipyl-7-ACA derivative intermediates. Alternatively the process may be carried out in a single one pot reaction without the formation of intermediates.

It was surprisingly found that the 3-thiolated derivative of cephalosporin C were very good substrates for the enzymatic reaction by D-amino acid oxidase in the presence of catalase.

3-thiolated-cephalosporin C derivatives of formula III (III)

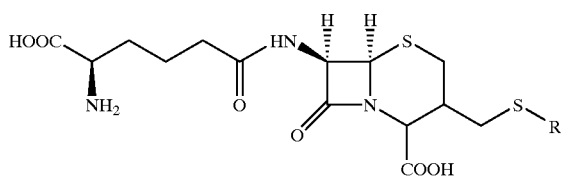

are prepared from cephalosporin C. The cephalosporin C solution may be in a purified or crude form. The cephalosporin C is in the form of any non-toxic salt of cephalosporin C.

The reaction of nucleophilic substitution in the 3' position is carried out in an aqueous medium, dissolving the heterocyclic thiol and any non-toxic cephalosporin C salt in water by addition of a basic compound which form a water soluble salt, such as alkali metal hydroxide, ammonium hydroxide or preferably alkali metal carbonate or bicarbonate. In general, in addition to salts produced as described above, any commercially available salt of cephalosporin C and of the heterocyclic thiols can be used in the process of this invention without changing the fundamentals of the process.

After dissolving the heterocyclic thiol and the cephalosporin C, in separate reaction vessels or jointly, both reactants are mixed together in the same reactor, before or after heating the solution to a temperature from about 65° C. to 80° C. at a pH value of between 5.5 and 7.0.

Once the reaction starts, the temperature and pH are maintained preferably at approximately 65° C. and 6.0 respectively, for a period of time of approximately 1 hour to 4 hours.

The heterocyclic thiol/cephalosporin C molar ratio is an important variable in the yield of the reaction and has to be optimised for each heterocyclic thiol used. Molar ratios are between 1.0 and 4.0, preferably at a molar ratio of approximately 4.

It was found that at these molar ratios the cephalosporin C remains quite stable with low β-lactam ring degradation, compared to a cephalosporin C solution without the thiol, which is completely degraded within 40 min at 80° C.

Once the cephalosporin C level is below 2% of the initial amount, the reaction mixture is cooled to a temperature from about 2° C. to about 10° C., with or without acidification at a pH of from pH 3.0 to 5.5, preferably approximately 5.2, with strong mineral acids, such as hydrogen halides or oxy acids.

This acidification step gives in some cases, crystallisation of the heterocyclic thiol, with the concomitant possibility of reuse for a new reaction.

After formation of the compound of formula III excess thiol groups are selectively removed which allows cephalosporin C derivatives of formula III to be prepared at very high purity levels and with very low levels (<0.2 mg/ml) of heterocyclic thiols present. A highly selective removal procedure with the strong anion exchanger Amberlite IRA-400 (manufactured by Rohm and Haas) is utilised. This process has several advantages. It allows compounds of Formula III to be used as a substrate without the poisoning of the enzymes in the next process step. As a result the enzymes may be used repeatedly. In addition the process does not require the use of toxic reagents or the need to isolate intermediates thereby providing a continuous process.

Different resins and types of chromatography may be used on an industrial scale.

Several resins were tested grouped in four classes of resins based on adsorption, hydrophilic-hydrophobic interaction, cation exchange, and anion exchange. All resins tested based on adsorption (Amberlite XAD-761, Amberlite 7HP, Amberlite 16 HP and Amberlite XAD-4) gave similar results, the eluate containing from 22% to 38% of the heterocyclic thiol. The hydrophobic-hydrophilic interaction resin Sephadex LH-20 did not retain any thiol (<5%). A similar situation was found with the cation exchangers Amberlite® IRC-50, IR-120 and IR-200. However, anion exchangers were found to have the best binding capacity for heterocyclic thiols ranging from 57–60% in the case of a weak anion exchanger (Amberlite IRA-93).

It was found that a strong microporous (gel-type I) anion (base) exchange resin Amberlite IRA-400 having an 8% cross linking containing function trialkyl benzyl ammonium groups gave the highest binding of heterocyclic thiols (from 92–98%) and low binding of the 3'-position heterocyclic thiomethyl cephalosporin C derivative (from 2–15%, less than 15% for the first cycle and less than 5% for the following cycles).

Such a microporous resin offers certain advantages. They are less fragile, require less care in handling and possess higher loading capacities. As they have no discrete pores solute ions diffuse through the particle to interact with exchange sites. The total exchange capacity of the mentioned resin is in the order of 1,4 meq/mL.

It was surprisingly found that Amberlite IRA-400 has less binding capacity for 3'-heterocyclic thiomethyl derivatives of cephalosporin C than for the same derivatives of glutaryl-7-ACA and 7-ACA. In fact the 3'-heterocyclic thiomethyl derivative of glutaryl-7-ACA produced with MND binds at a level of 76.3% to the column. The same result is found with 3'-heterocyclic thiomethyl derivative of 7-ACA, with MMTD, which binds at a level of 92.7% to the column. This unexpected behaviour of Amberlite IRA400 with these three related β-lactam compounds appears to result from the presence of an ionisable amino group in the 5 position of the side chain of cephalosporin C compared with glutaryl-7-ACA and 7-ACA.

The removal of heterocyclic thiols by the process of the invention is particularly advantageous on an industrial scale as the eluate of the column can be used for enzymation without isolation of the modified cephalosporin C and represents a new concept in the field of cephalosporin intermediates wherein the impurities are bound to the column and the β-lactam derivative is simply eluted by water.

Once the β-lactam derivative is eluted (less than 5% remains bound), the column is typically regenerated with a 1.5 N solution of a strong mineral acid, such as hydrogen halide containing variable amounts of an organic solvent, preferably 10–20% acetonitrile. When the concentration of the thiol in the eluate is higher than 0.2 mg/ml, a strong regeneration using 3 N HCl and 40% acetonitrile may be carried out. Alternatively regeneration with 1.5M HCl and 1.0 N NaOH is also possible.

After elution of the heterocyclic thiol, the thiol is concentrated and reused. The column is rinsed with deionised water to remove excess regenerant before the next cycle. The first bed volume of the rinse should be performed at the flow rate used for regeneration. The remainder is run at the adsorption flow rate.

Compounds of formula III are enzymatically converted into new stable α-ketoadipyl-7-ACA derivatives of formula IV by an immobilised enzyme system.

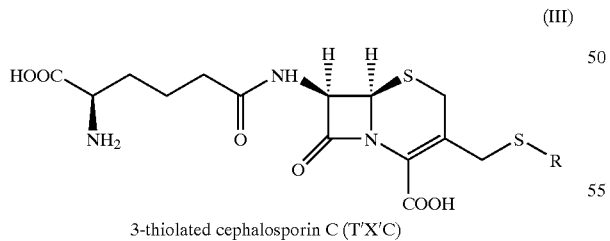

(III)

3-thiolated cephalosporin C (T'X'C)

wherein R is a heterocyclic group comprising at least a nitrogen atom with or without a sulphur or oxygen.

The use of co-immobilised enzymes (D-AAO and catalase) on the same solid support allows a better hydrogen peroxide removal than with separate supports. The biocatalyst with both enzymes is easily recoverable from the reaction medium and reusable a large number of times. This is a necessary and indispensable factor for an industrial process.

A further industrial advantage of the invention is the easy transfer of the chemical solution comprising a compound of formula III, after chromatography in a strong anionic exchange resin (Amberliteo® IRA-40, manufactured by Rohm and Haas) to an enzymatic reactor containing the co-immobilised enzymes. This enables the process to be conducted continuously with a single liquid stream from cephalosporin C to compound IV.

The enzymatic stage may be carried out in different ways:
1) Chemical reaction without removal of the excess of the heterocyclic thiol and oxidative deamination with immobilised D-AAO. Under these conditions, compound IV is accumulated to about 35 to 40% of total β-lactams, which is higher than the 5 to 10% accumulation of α-ketoadipyl-7-ACA produced when unmodified cephalosporin C is used. Thus indicating the stability of the compound IV.
2) The same as 1) including soluble catalase. Under these conditions, the level of compound IV reaches 70 to 75% of total β-lactams in solution with less than 10% of 3-thiolated glutaryl-7-ACA (T'X'G). However the immobilised enzyme and catalase are poisoned within a few cycles by the presence of high levels of heterocyclic thiol (□1 mg/mL).
3) Chemical reaction with removal of the excess of the heterocyclic thiol by ion exchange chromatography and co-immobilisation of D-AAO and catalase on the same solid support. Under these conditions, compound IV is accumulated from about 80% to 90% of total β-lactams, depending on the pH used. At pH values of approximately 6.5, compound IV is more stable reaching 90% accumulation but the D-AAO is less active (more biocatalyst is needed). At pH values near 7.25, the enzyme is more active but compound IV is less stable, obtaining a 80% accumulation. The preferred pH is pH 6.75, which provides the lowest loss in D-AAO activity with good stability of compound IV.

From the above it is clear that approach 3) is advantageous versus the others but several parameters have to be taken into account to produce a good biocatalyst with the two enzymes (D-AAO and catalase) co-immobilised:

a) The source of both enzymes. D-AAO in this invention is obtained from *Trigonopsis variabilis* CBS 4091 obtained from the Spanish collection of microorganisms (CECT, Valencia, Spain). This yeast is grown under the conditions to induce D-AAO (Kubicek et al, *J. Appl. Biochem.* 7; 104, 1985) and the enzyme was purified by ammonium sulfate fractionation between 30%–55% as described by Szwjcer et al (*Biotechnol. Lett.* 7, 1, 1985). Amino acid oxidases may also be sourced from *Rodotorula gracilis*. Catalase from *Micrococcus lisodeikticus* is obtained from a commercial source (Fluka, Madrid, Spain), but it may also be sourced from *Aspergillas niger*.

b) The solid support used. Several carriers are available to immobilise enzymes. The most popular are: Amberlite® IRA 900 (strongly basic polystyrene resin with a quaternary amine function), Duoliteo® A365 (weakly basic polystyrene resin with primary functional groups), Duoliteo® A568 (moderately basic polycondensed phenolformaldehyde resin), BrCN-activated Sepharose®, vinyl Sepharose® and Eupergit C® (based on a polyacrylic structure and in particular with oxirane terminal groups). Among Eupergit, two classes are commercialised (Röhm Pharma) C and C250L, the latter type is particularly suitable for binding high molecular weight enzymes, since its contents in oxirane groups are at least 0.36% compared with the 0.93% in Eupergit C. This C250L type show outstanding properties when employed in industrial biocatalytic processes. The morphology of the carrier, i.e., its narrow particle size distribution (200 μm) and high mechanical stability accounts for their good properties in stirred-tank reactors. It is not mechanically destroyed in stirred systems and filtration at the end of the reaction cycle is quick and very easy to perform. Changes in the pH and ionic strength have no effect on swelling of the matrix. In addition, this Eupergit C250L has never been used to immobilise D-amino acid oxidase and catalase.

c) The ratio catalase units/D-AAO units. This ratio is normally bigger than 100, but for efficient hydrogen peroxide removal the ratio is preferably about 1500. One unit of D-AAO is defined as the amount of enzyme that consumes a μmol of $O_2$ per minute using cephalosporin C as substrate at pH 8.0 and 25° C. One unit of catalase is defined as the amount of enzyme that decomposes 1 μmol of hydrogen peroxide per minute at pH 7.0 and 25° C.

d) The procedure of co-immobilisation. Several immobilisation protocols can be used. The one chosen in this invention is a modification of the method described by Cramer and Steckham (Tetrahedron, 45, 14645, 1997) for the co-immobilisation of L-α-glycerolphosphate oxidase with catalase. Typically 100 mg of Eupergit® C250L are suspended in 1.5 ml of coupling buffer (1.0 M potassium phosphate buffer pH 8.0) in an Erlenmeyer flask. Then 10–40 U of D-AAO and 10–20 kU of catalase (Fluka, cat# 60634) are added slowly. The mixture is incubated for 16 h with gentle shaking. After the immobilisation procedure, the beads are separated by a glass frit and washed for several times using a 100 mM potassium phosphate buffer pH 7.0 at 4° C.

Once the co-immobilisation is carried out, the enzymatic conversion of the compound III into compound IV is carried out in an aqueous solution of compound III containing from about 0.0016 to 0.004 moles and with less than 0.2 mg/ml of the heterocyclic thiol. This solution is obtained after passing the solution comprising 3-thiolated cephalosporin C (compound III) and remaining heterocyclic thiol used in the nucleophilic displacement of 3 acetoxy group of cephalosporin C through a column of a strong anion exchanger, such as Amberlite® IRA-400 (Rohm and Hass). The pH of the eluate is adjusted to pH about 6.5 to 8.0, preferably to pH 6.75, due to the instability of cephalosporanic compounds at basic pH values.

The solution comprising compound III as described above is fed into a bioreactor, containing wet Eupergit C250L with co-immobilised D-AAO/catalase, usually D-AAO from 20–40 U/g, and catalase, usually from 10–30 kU/g. The reaction temperature can be fixed from 15° C. to 35° C., and is normally fixed at 20° C.

The molecular oxygen, needed for the oxidative deamination, is blown into solution by a bottom diffuser at a flow rate from 0.01 to 1 volume/volume of solution/minute, preferably at 0.1 vvm under a suitable mechanical stirring of about 400 rpm. This bioreactor design is preferred versus a percolation column containing the immobilised enzymes to avoid the diffusional problems of the molecular oxygen, which reduce the yield of compound IV. The pH is titrated to pH 6.75 by dosing a concentrated organic or inorganic base, preferably 3 M ammonia, by means of an autotitrator.

The conversion is controlled by HPLC and when the conversion of compound III is greater than 97%, the reaction is stopped and the solution filtered off. The time required for such conversion is of the order 0.5 to 3 hours, depending on the operating conditions, but usually approximately 1 hour.

Isolation of compound IV, when required, is carried out by decreasing the pH of the above solution to a pH of about 4.5 to 6.0, preferably 5.0 with the same base used during the enzymatic reaction, and loading into a column packed with the adsorptive resin Amberlite XAD-2. The elution of compound IV is carried out with water at a flow rate of 2–3 bed volumes per hour. Fractions containing the compound IV with a HPLC purity higher than 90–95% are pooled and lyophilised.

Compounds of formula IV are subsequently converted into compounds of formula I by enzymation with glutaryl-7-ACA acylase.

The process of the invention for preparing compounds of formula I from cephalosporin C may also be carried out in a single one pot reaction. In this case filtrate from an anion exchange column comprising compounds of formula III is enzymatically converted into compounds of formula I by an immobilised enzyme system comprising D-AAO and catalase in the presence of glutaryl-7-ACA acylase. Compounds of formula I have been prepared in this way with a HPLC of approximately 95%. The process is easy and efficient to carry out.

Using both processes (one-pot or two-steps) of the invention, 3-thiolated-7-ACA derivatives are easily and economically prepared. These compounds may by subsequent enzymation with penicillin G acylase for example, be used for the preparation of semisynthetic β-lactam antibiotics. The β-lactam antibiotics may include any one or more of cefazolin, cefazedone, cefoperazone, cefamandol, cefatriazine, cefotiam and ceftriaxone.

The following examples are meant to illustrate the invention without limitation as to its generality.

Examples 1 to 5 illustrates the preparation of 3-thiolated-7-ACA derivatives of formula III from cephalosporin C.

Examples 6 to 8 illustrate the enzymatic process for the preparation of a 3-thiolated α-ketoadipyl-7-ACA derivatives of formula IV from 3-thiolated cephalosporin C derivatives of formula III.

Examples 9 to 11 illustrate the enzymatic process for the preparation of 3-thiolated-7-ACA derivatives (TXA) of formula I from 3-thiolated derivatives of formula III via the formation of stable α-ketoadipyl-7-ACA derivatives of formula IV.

Examples 12 to 14 illustrate the enzymatic process for the preparation of 3-thiolated-7-ACA derivatives of formula I from 3-thiolated derivatives of formula III in a single step (one pot).

EXAMPLE 1

Preparation of 7-β-(5-amino-5-carboxypentanamido)-3-(5-methyl-1,3,4-thiadiazole-2-yl thiomethyl)-3-cephem-4-carboxylic acid (TDC)

To a glass-lined reactor containing 600 mL of deionised water, 31.73 g (0.24 moles) of 2-mercapto-5-methyl-1,3,4-thiadiazole (MMTD) were added and the reactor was heated with stirring to a temperature of about 65° C. The pH of the mixture was adjusted to pH of about 6.0 by the addition of about 10 g of sodium carbonate.

In a separate glass-lined flask, a solution of concentrated sodium cephalosporin C (98% purity by HPLC) was prepared by dissolving 33.23 g of sodium cephalosporin C (75% free acid, 0.06 moles) in 200 ml of water. When the MMTD was dissolved, the concentrated cephalosporin C solution was added and the mixture was stirred at approximately 65° C. for 240 minutes, controlling the reaction kinetic until the level of cephalosporin C was below 2%. The following reaction kinetics were found:

| Time (min) | Cephalosporin C (moles) | TDC (moles) | MMTD (moles) |
|---|---|---|---|
| 0 | 0.06 | 0.00 | 0.24 |
| 120 | 0.01 | 0.039 | 0.20 |
| 240 | 0.0012 | 0.042 | 0.195 |

The reaction mixture was then cooled to about 4° C., where the crystallisation of the excess of MMTD begins. The pH was acidified with stirring (150 rpm) to a pH 5.2 with 37% hydrochloride acid and left under slow stirring (50 rpm) for 60 minutes for the completion of crystallisation.

The precipitated MMTD was filtered and dried at 35° C. under vacuum. 23 g of recovered MMTD was obtained (purity 99% by HPLC) with a recovery yield of about 95%.

The filtrate (825 ml) containing 0.042 moles of the TDC and MMID 0.016 moles was adjusted to pH 7.25 with 3 M ammonia and loaded onto an Amberlite IRA-400 column in chloride cycle (bed volume equal to 180 ml) covered with deionised water at flow rate 20 ml/min. Once loaded, the column was washed with deionised water (ca 100 ml) until 97% recovery of loaded TDC with a 94% purity by HPLC. The pH of the effluent was about 5.4 and was neutralised to 7.0 with 3 M ammonia. The remaining MMTD was 0.0009 moles (<0.2 mg/ml), which is less than 6% of the remaining MMTD after its crystallisation by decreasing the pH. With this low level of MMTD (<1% of the original MMTD after chemical reaction), enzymation of TDC is possible.

Typically the column is regenerated with 1 L of 1.5 M HCl containing 10% acetonitrile and rinsed free of the excess regeneration by washing with 2 liters of deionised water. When required (MMTD>0.2 mg/ml) the resin can be subjected to a strong regeneration using 1 liter of 3 M HCl with 40% acetonitrile. Alternatively, regeneration with 1.5 M HCl and 1.0 N NaOH is also possible.

To further characterise the TDC solution at pH 5.0, it was loaded onto a Amberlite XAD-2 adsorption column and the column was washed with water. After washing, the resin was eluted with water, and 25 ml portions were pooled. A fraction containing 98.5% TDC by HPLC was lyophylised and subjected to analysis:

Elemental Analysis for the product $C_{17}H_{20}N_5O_6S_3 \cdot 2H_2O$ (TDC), calculated C 37.42; H 4.43; N 12.84; S 17.63; found 37.27; H 4.3; N 13.11; S 17.51.

$^1$H-NMR (DMSO/DCl) (δ ppm): 1.57 (m, 2H, —CH$_2$—); 1.63 (m, 2H, —CH$_2$—); 2.18 (m, 2H, —CH$_2$—); 2.64 (s, 3H, CH$_3$); 3.55, 373 (J=18 Hz, 2H, —CH$_2$—); 3.83 (t, 1H, —CH—); 4.18–4.46 (d, J=13 Hz, 2H, —CH$_2$—); 5.02 (d, J=3 Hz, 1H, C-6); 5.6 (d, J=3 Hz, 1H, C-7).

EXAMPLE 2

COMPARATIVE EXAMPLE

Preparation of 7-β-(5-amino-5-carboxypentanamido)-3-(5-methyl-1,3,4-thiadiazole-2-ylthiomethyl)-3-cephem-4-carboxylic acid on Different Columns The TDC derivative was prepared as described in Example 1 and the filtrate containing it was loaded onto different types of resins.

The following data was obtained after washing with 100 ml of water in the first cycle of column usage:

| Resin | Type | Eluted TDC (%) | Eluted MMTD (%) |
|---|---|---|---|
| Amberlite IRA-400 | Strong anion exchanger | 86 | 2 |
| Diaion SA10A | Strong anion exchanger | 67 | 15 |
| Amberlite IRA93 | Weak anion exchanger | 87 | 45 |
| Amberlite IRC-50 | Weak cation exchanger | 93 | 92 |
| Amberlite IRC-200 | Strong cation exchanger | 73 | 98 |
| Amberlite XAD-761 | Adsorption | 86 | 22 |
| Amberlite XAD-7 HP | Adsorption | 77 | 23 |
| Amberlite XAD-16 HP | Adsorption | 75 | 35 |
| Amberlite XAD-4 | Adsorption | 68 | 25 |
| Amberlite XAD-1180 | Adsorption | 78 | 38 |
| Sephadex LH-20 | Hydrophobic hydrophilic | 98.5 | 95 |

Amberlite IRA-400 gave the best results. A high elution of TDC was observed with low elution of MMTD. Using other anion exchange columns higher amounts of MMTD were also eluted. The other anion exchangers showed a high dual binding of thiol and TDC.

EXAMPLE 3

Specificity of TDC for Amberlite IRA-400

The glutaryl-7-ACA derivative (TDG) and 7-ACA derivative (7-TDA) were prepared as in Example 1 using glutaryl-7-ACA and 7-ACA as starting material. The following data was obtained from the filtrate of the Amberlite IRA-400.

| Resin | Compound in the elute | TDG or TDA eluted (%) | MMTD eluted (%) |
|---|---|---|---|
| Amberlite IRA-400 | TDG | 23.7 | 3.0 |
|  | TDA* | 7.3 | 1.4 |

*At pH 7.8 to avoid any precipitation of TDA into the column.

In contrast to TDC, both TDG and TDA appear to remain bound to the Amberlite IRA400 as well as the MMTD.

EXAMPLE 4

Preparation of 7-β-(5-amino-5-carboxypentanamido)-3-[(1-methyl-1H-tetrazol-5-yl)-thiomethyl]-cephalosporanic acid (TZC)

To a glass-lined reactor containing 600 mL of deionised water 28.16 g (0.24 moles) of 5-mercapto-1-methyltetrazole (MMTZ) were added and the reactor was heated with stirring to a temperature of about 70° C. The pH of the mixture was adjusted to a pH of about 5.7–5.8 by the addition of about 12 g of sodium carbonate.

In a separate glass-lined flask, a solution of concentrated sodium cephalosporin C was prepared by dissolving 33.23 g of sodium cephalosporin C (75% free acid, 0.06 moles purity 98% by HPLC) in 200 ml of water. When the MMTZ was dissolved, the concentrated cephalosporin C solution was added and the mixture was stirred at about 70° C. for 120 minutes, controlling the reaction kinetic until the level of cephalosporin C was below 3%.

| Time (min) | Cephalosporin C (moles) | TZC (moles) | MMTZ (moles) |
|---|---|---|---|
| 0 | 0.06 | 0 | 0.24 |
| 120 | 0.0017 | 0.040 | 0.19 |

The reaction mixture was cooled at about 4° C., but crystallisation of the excess of MMTZ did not start, even when the pH was decreased. The solution containing 0.04 moles of the TZC derivative from MMTZ and 0.19 moles of MMTZ was adjusted to pH 7.25 with 3 M ammonia and loaded onto an Amberlite IRA-400 column in chloride cycle (bed volume equal to 150 ml) covered with deionised water at flow rate 20 ml/min. After the first pass through the column the remaining MMTZ was higher than 13% of the initial (0.032 moles).

For this reason, the eluate was loaded onto another Amberlite IRA-400 (bed volume equal to 60 ml) column under the same conditions as described above to decrease the level of MMTZ.

Once loaded, the column was washed with deionised water (ca 90 ml) until 97% recovery of loaded TZC with a 87% purity by HPLC. The pH of the effluent was about 5.4 and was neutralised to pH 7.0 with 3 M ammonia. The remaining MMTZ concentration was 0.0013 moles, which is less than 1% of the original MMTZ after chemical reaction. With this low level of MMTZ, enzymation of the derivative is possible without poisoning the enzyme.

The columns were regenerated with 1 L of 1.5 M HCl containing 10% acetonitrile and rinsed free of the excess regeneration by washing with 2 liters of deionised water. Alternatively, regeneration with 1.5 M HCl and 1.0 N NaOH is also possible.

EXAMPLE 5

Preparation of 7-β-(5-amino-5-carboxypentanamido)-3-cephalosporanic acid (TTC)

To a glass-lined reactor containing 600 ml of deionised water 37.96 g (0.24 moles) of 2,5-dihydro-3-mercapto-2-methyl-5,6-dioxo-1,2,4-triazine (here below indicated as TTZ) were added and the reactor was heated with stirring to a temperature of approximately 75° C. The pH of the mixture was adjusted to pH of approximately 6.7 by the addition of approximately 12 g of sodium carbonate.

In a separate glass-lined flask, a solution of concentrated sodium cephalosporin C was prepared by dissolving 33.23 g of sodium cephalosporin C (75% free acid, 0.06 moles, purity 98% by HPLC) in 200 ml of water. When the TTZ was dissolved, the concentrated cephalosporin C solution was added and the mixture was stirred at approximately 75° C. for 75 minutes, controlling the reaction kinetic until the level of cephalosporin C was below 2%.

| Time (min) | Cephalosporin C (moles) | TZC (moles) | TTC (moles) |
|---|---|---|---|
| 0 | 0.06 | 0 | 0.24 |
| 75 | 0.0011 | 0.036 | 0.19 |

The reaction mixture was cooled at approximately 4° C., but crystallisation of the excess of TTZ does not start, even when the pH was decreased. The solution containing the 0.036 moles of TTC and 0.19 moles of TTZ was adjusted to pH 7.25 with 3 M ammonia and loaded onto an Amberlite IRA-400 column in chloride cycle (bed volume equal to 209 ml) covered with deionised water at flow rate 20 ml/min. After the first column the remaining TTZ was 0.015 moles.

For this reason, the eluate was loaded onto another Amberlite IRA-400 column (with the same bed volume) under the same conditions as described above to decrease the level of TTZ.

Once loaded, the column was washed with deionised water (ca 120 ml) until 60% recovery of loaded TTC with a 90% purity by HPLC. The pH of the effluent was about 5.4 and was neutralised to pH 7.0 with 3 M ammonia. The remaining TTZ concentration was 0.00096 moles, which is less than 1% of the original TTZ after chemical reaction. With this level of TTZ, enzymation of the derivative is possible without poisoning the enzyme.

The columns were regenerated with 1 L of 1.5 M HCl containing 10% acetonitrile and rinsed free of the excess regeneration by washing with 2 liters of deionised water. Alternatively, regeneration with 1.5 M HCl and 1.0 N NaOH is also possible.

EXAMPLE 6

Preparation of 7β-(5-carboxy-5-oxopentamide)-3-[(5-methyl-1,3,4-thiadiazole-2-yl)-thiomethyl] cephalosporanic acid (TDK)

A filtrate (80 ml) from the strong anion exchanger Amberlite® IRA400 containing 0.0035 moles of 7β-(5-amino-5-carboxypentamido)-3-[(5-methyl-1,3,4-thiadiazole-2-yl)-thiomethyl]cephalosporanic acid (TDC) with 94.3% purity (HPLC) and less than 0.2 mg/mL of 2-mercapto-5-methyl-1,3,4-thiadiazole (MMTD) was adjusted to pH 6.75 with 3 M ammonia.

The TDC solution was fed into a 0.125 liter stirred glass vessel with 30.76 g of wet Eupergit C250L with a co-immobilised D-amino acid oxidase/catalase system (11.77 U of DAAO/g and 15 kU of catalase/g).

The conversion was performed at 20° C., 400 rpm and with an oxygen flow through a bottom diffuser of 0.1 vol/vol/min at 1 bar absolute pressure. The pH was titrated to pH 6.75 with 3 M ammonia by an autotitrator.

The conversion was controlled by HPLC in a reverse phase column Nucleosil 120 3-C18 125×8×4 mm. The mobile phase was 20 mM acetate ammonium pH 5.5 containing 4% acetonitrile at 1 mi/min with a 260 nm detection. The TDC appeared at 7.0 minutes, the TDK at 8.5 min and the 3-thiolated glutaryl-7-ACA intermediate (TDG) at 11.5 min.

Representative samples of the reaction mixture except for the enzyme were taken and the results obtained are given as percentage of total β-lactams in the following table:

| Time (min.) | TDC [%] | TDK [%] | TDG [%] | side products [%] |
|---|---|---|---|---|
| 0 | 94.3 | 0.0 | 0.0 | 5.7 |
| 15 | 68.3 | 25.9 | 0.0 | 5.8 |
| 60 | 2.6 | 89.9 | 0.9 | 6.6 |

When the % of remaining TDC was less than 3%, the reaction was stopped and the reaction solution was filtered off.

To isolate TDK, the resulting solution was adjusted to pH 5.0 with 3 M ammonia and passed through a column packed with 40 g of the adsorptive resin Amberlite XAD-2 (68.7 ml of bed volume). Elution was carried out with water at a flow rate of 200 ml/h (about 3 bed volumes per hour). Fractions of 25 ml containing TDK with a purity≧95% (HPLC) were pooled and lyophilised to obtain the target product as a solid to further analyse it. After the elution process, the adsorbent surface is reactivated by applying 2 bed volumes of regeneration solution (25% methanol in water at 3 bed volumes per hour). Before the column can be used again, this solution is removed from the column. After equilibration with water in excess (about 15 bed volumes), the column is ready for re-use.

$^1$H-NMR (DMSO) (δ ppm): 1.66 (m, 2H, —$CH_2$—); 2.16 (t, 2H, —$CH_2$—); 2.50 (t, 2H, —$CH_2$—); 2.65 (s, 3H, —$CH_3$—); 3.34–3.58 (J=17.4 Hz, 2H, —$CH_2$—); 4.31–4.48 (J=12.1 Hz, 2H, —$CH_2$—); 4.94 (J=5.1 Hz, 1H, C-6); 5.5 (d,d, J=5.1 Hz, J=8.4 Hz, 1H, C-7).

EXAMPLE 7

Preparation of 7β-(5carboxy-5-oxopentanamide)-3-[(1-methyl-1H-tetrazol-5-yl)-thiomethyl]-cephalosporanic acid (TZK)

A filtrate (100 ml) from the strong anion exchanger Amberlite® IRA-400 containing 0.0039 moles of 7-(5'-amidoadipamido)-3-[(1-methyl-1H-tetrazol-5-yl)-thiomethyl]-cephalosporanic acid (TZC) with 90.1% purity (HPLC) and less than 0.2 mg/ml of 5-mercapto-1-methyltetrazole (MMTZ) was adjusted to pH 6.75 with 3 M ammonia.

The TZC solution was fed into a 0.125 liter stirred glass vessel with 30.76 g of wet Eupergit C250L with a coimmobilised D-amino acid oxidase/catalase system (11.77 U of DAAO/g and 15 kU of catalase/g).

The conversion was performed at 20° C., 400 rpm and with an oxygen flow through a bottom diffuser of 0.1 vol/vol/min at 1 bar absolute pressure. The pH was titrated to pH 6.75 with 3 M ammonia by an autotitrator.

The conversion was controlled by HPLC on a reverse phase column Nucleosil 120 3—C18 125×8×4 mm. The mobile phase was 20 mM ammonium acetate pH 5.5 containing 4% acetonitrile at 1 ml/min with a 260 nm detection. The TZC appeared at 3.0 minutes, the TZK at 3.6 min and the 3-thiolated glutaryl-7-ACA intermediate (TZG) at 4.6 min.

Representative samples of the reaction mixture except for the enzyme were taken and the results obtained are given as percentage of total β lactams in the following table:

| Time (min.) | TZC [%] | TZK [%] | TZG [%] | Side products [%] |
|---|---|---|---|---|
| 0 | 90.1 | 0.0 | 0.0 | 9.9 |
| 15 | 31.3 | 57.8 | 0.8 | 10.1 |
| 45 | 0.4 | 87.3 | 1.6 | 10.7 |

When the % of remaining TZC was less than 3%, the reaction was stopped and the reaction solution was filtered off.

To isolate the TZK, the resulting solution was adjusted to pH 5.0 with 3 M ammonia and passed through a column packed with 40 g of the adsorptive resin Amberlite XAD-2 (68.7 ml of bed volume). Elution was carried out with water at a flow rate of 200 ml/h (about 3 bed volumes per hour). Fractions of 25 ml containing the TZK with a purity≧93% (HPLC) were pooled and then lyophilised to obtain the target product as a solid to further analyse it. After the elution process, the adsorbent surface is reactivated applying 2 bed volumes of regeneration solution (25% methanol in water at 3 bed volumes per hour). Before the column can be used again, this solution is removed from the column. After equilibration with water in excess (about 15 bed volumes), the column is ready for re-use.

$^1$H-NMR (DMSO) (δ ppm): 1.61 (m, 2H, —$CH_2$—); 2.12 (t, 2H, —$CH_2$—); 2.45 (t, 2H, —$CH_2$—); 3.33–3.56 (J=17.4 Hz, 2H, —$CH_2$—); 3.86 (s, 3H, —$CH_3$—); 4.18–4.35 (J=12.6 Hz, 2H, —$CH_2$—); 4.88 (d, J=4.8 Hz, 1H, C-6); 5.46 (d,d, J=4.8 Hz, J=8.2 Hz, 1H, C-7).

EXAMPLE 8

Preparation of 7β-(5carboxy-5-oxopentanamide)-3-[(1,2,5,6-tetrahydro-2-methyl-5,6-dioxo-1,2,4-triazin-3-yl)-thiomethyl]-cephalosporanic acid (TTK)

A filtrate (50 ml) from the strong anion exchanger Amberlitee® IRA400 containing 0.0016 moles of 7β-(5-amino5-carboxypentamido)-3-[(1,2,5,6-terahydro-2methyl-5,6-dioxo-1,2,4-triazin-3-yl)-thiomethyl]-cephalosporanic acid (TTC) with 89.86% purity (HPLC) and less than 0.2 mg/ml of 2,5-dihydro-3-mercapto-2-methyl-5,6-dioxo-1,2,4-triazine (TTZ) was adjusted to pH 6.75 with 3 M ammonia.

The TTC solution was fed into a 0.125 liter stirred glass vessel with 30.76 g of wet Eupergit C250L with a co-immobilised D-amino acid oxidase/catalase system (11.77 U of DAAO/g and 15 kU of catalase/g).

The conversion was performed at 20° C., 400 rpm and with an oxygen flow through a bottom diffuser of 0.1 vol/vol/min at 1 bar absolute pressure. The pH was titrated to pH 6.75 with 3 M ammonia by an autotitrator.

The conversion was controlled by HPLC in a column Eclipse® XDB-C8 5 μm 4.6×150 mm. The mobile phase was 35% methanol in 10 mM TBHS (tetrabutylammonium hydrogen sulfate) and 15 mM potassium dihydrogen phosphate at 1 ml/min with 260 nm. The TTC appeared at 2.6 minutes, the 3-thiolated glutaryl-7-ACA intermediate (TTG) at 5.5 min and the TTK at 6.6 min.

Representative samples of the reaction mixture except for the enzyme were taken and the results obtained are given as percentage of total μ-lactams in the following table:

| Time (min.) | TTC [%] | TTK [%] | TTG [%] | Side products [%] |
|---|---|---|---|---|
| 0 | 89.86 | 0.00 | 0.00 | 10.14 |
| 30 | 17.26 | 71.37 | 0.89 | 10.48 |
| 60 | 0.55 | 86.52 | 1.88 | 11.05 |

When the % of remaining TTC was less than 3%, the reaction was stopped and the reaction solution was filtered off.

To isolate the TTK, the resulting solution was adjusted to pH 5.0 with 3 M ammonia and passed through a column packed with 40 g of the adsorptive resin Amberlite XAD-2 (68.7 ml of bed volume). Elution was carried out with water at a flow rate of 200 ml/h (about 3 bed volumes per hour). Fractions of 25 ml containing the TTK with a purity≧90% (HPLC) were pooled and then lyophilised to obtain the target product as solid to further analyse it. After the elution process, the adsorbent surface is reactivated by applying 2 bed volumes of regeneration solution (25% methanol in water at 3 bed volumes per hour). Before the column can be used again, this solution is removed from the column. After equilibration with water in excess (about 15 bed volumes), the column is ready for re-use.

$^1$ H—NMR (D$_2$O)(δ ppm): 1.89 (m, 2H, —CH$_2$—); 2.38 (t, 2H, —CH$_2$—); 2.81 (t, 2H, —CH$_2$—); 3.45–3.72 (J=17.7 Hz, 2H, —CH$_2$—); 3.65 (s, 3H, —CH3—); 4.05–4.34 (J=13.2 Hz, 2H, —CH$_2$—); 5.10 (d, J=4.7 Hz, 1H, C-6); 5.62 (d, J=4.7 Hz, 1H, C-7).

EXAMPLE 9

Synthesis of 7-amino-3-[(5-methyl-1,3,4-thiadiazol-2-yl)-thiomethyl]-cephalosporanic acid (TDA)

A filtrate (50 ml) from the strong anion exchanger Amberlite® (IRA-400 containing 0.0011 moles of 7β-(5-amino-5-carboxypentamido)-3-[(5-methyl-1,3,4-thiadiazole-2-yl)-thiomethyl]cephalosporanic acid (here below indicated as TDC) with 94.01% purity (HPLC) and less than 0.2 mg/ml of 2-mercapto-5-methyl-1,3,4-thiadiazole (MMTD) was adjusted to pH 6.75 with 3 M ammonia.

The TDC solution was fed into a 0.125 liter stirred glass vessel with 16 g of wet Eupergit C250L with a co-immobilised D-amino acid oxidase/catalase system (25 U of DAAO/g and 30 kU of catalase/g).

The conversion was performed at 20° C., 400 rpm and with an oxygen flow through a bottom diffuser of 0.1 vol/vol/min at 1 bar absolute pressure. The pH was titrated to pH 6.75 with 3 M ammonia by an autotitrator.

The conversion was controlled by HPLC in a reverse phase column Eclipse XDB-C8 150 mm×4.6 mm ID×5 μm; the mobile phase was 10 mM tetrabutylammonium hydrogen sulfate, 15 mM potassium dihydrogen phosphate, pH 6.5 containing 35% methanol at 1 ml/min with a 260 nm detection. The TDC appeared at 3.0 min, the TDK at 10.9 min and the TDG at 8.1 min., respectively.

Representative samples of the reaction mixture except for the enzyme were taken and the result obtained are reported as percentage of total β-lactams in the following table:

| Time (min) | % TDC | % TDK | % TDG | % Side Products |
|---|---|---|---|---|
| 0 | 94.57 | 0.00 | 0.00 | 9.43 |
| 15 | 53.86 | 36.19 | 1.66 | 8.29 |
| 60 | 0.00 | 88.27 | 5.48 | 6.25 |

When the % of remaining TDC was smaller than 3%, the reaction was stopped and the reaction solution, containing TDK with a HPLC purity of 88.27%, was filtered off, and adjusted to pH 7.25 with 3 M ammonia.

The TDK solution was fed into a 0.125 liter stirred glass vessel with 23 g of wet Glutaryl-7-ACA Acylase (87 U/g). The conversion was performed at 20° C., 400 rpm at 1 bar absolute pressure. The pH was titrated to pH 7.25 with 3 M ammonia by an autotitrator.

The conversion was controlled by HPLC under the above-mentioned conditions. The TDA appeared at 4.1 minutes. Representative samples of the reaction mixture except for the enzyme were taken and the result obtained are reported as percentage of total β-lactams in the following table:

| Time (min) | % TDK | % TDG | % TDA | % Side Products |
|---|---|---|---|---|
| 0 | 88.27 | 5.48 | 0.0 | 6.25 |
| 30 | 11.82 | 3.50 | 73.76 | 10.92 |
| 60 | 2.6 | 0.0 | 88.59 | 8.81 |

When the % of remaining TDK was smaller than 3%, the reaction was stopped. The reaction solution contained TDA with a HPLC purity of 88.59%.

EXAMPLE 10

Synthesis of 7-amino-3-[(1-methyl-1H-tetrazol-5-yl)-thiomethyl]-cephalosporanic acid (TZA)

A filtrate (50 mL) from the strong anion exchanger Amberlite® IRA-400 containing 0.00195 moles of 7β(5-amino-5-carboxypentamido)-3-[(1-methyl-1H-tetrazol-5-yl)-thiomethyl]cephalosporanic acid (TZC) with 91.74% purity (HPLC) and less than 0.2 mg/ml of 5-mercapto-1-methyltetrazole (MMTZ) was adjusted to pH 6.75 with 3 M ammonia.

The TZC solution was fed into a 0.125 liter stirred glass vessel with 16 g of wet Eupergit C250L with a coimmobilised D-amino acid oxidase/catalase system (25 U of DAAO/g and 30 kU of catalase/g).

The conversion was performed at 20° C., 400 rpm and with an oxygen flow through a bottom diffuser of 0.1 vol/vol/min at 1 bar absolute pressure. The pH was titrated to pH 6.75 with 3 M ammonia by an autotitrator.

The conversion was controlled by HPLC in a reverse phase column Eclipse XDB-C8 150 mm×4.6 mm ID×5 [lm; the mobile phase was 10 mM tetrabutylammonium hydrogen sulfate, 15 mM potassium dihydrogen phosphate, pH 6.5 containing 35% methanol at 1 ml/min with a 260 nm detection. The TZC appeared at 2.1 minutes, the TZK at 5.0 min and the TZG at 4.3 min, respectively.

Representative samples of the reaction mixture except for the enzyme were taken and the result obtained are reported as percentage of total β-lactams in the following table:

| Time (min) | % TZC | % TZK | % TZG | % Side products |
|---|---|---|---|---|
| 0 | 91.74 | 0.00 | 0.00 | 8.26 |
| 15 | 26.23 | 58.78 | 5.13 | 9.86 |
| 45 | 0.59 | 82.42 | 5.34 | 11.65 |

When the % of remaining TZC was smaller than 3%, the reaction was stopped and the reaction solution, containing TZK with a HPLC purity of 82.42%, was filtered off, and adjusted to pH 7.25 with 3 M ammonia.

The TZK solution was fed into a 0.125 liter stirred glass vessel with 23 g of wet Glutaryl-7-ACA Acylase (87 U/g). The conversion was performed at 20° C., 400 rpm at 1 bar absolute pressure. The pH was titrated to pH 7.25 with 3 M ammonia by an autotitrator.

The conversion was controlled by HPLC under the above-mentioned conditions. The TZA appeared at 2.5 min. Representative samples of the reaction mixture except for the enzyme were taken and the result obtained are reported as percentage of total β-lactams in the following table:

| Time (min) | % TZK | % TZG | % TZA | % Side products |
|---|---|---|---|---|
| 0 | 82.42 | 5.34 | 0.00 | 12.24 |
| 15 | 41.52 | 5.05 | 39.26 | 14.17 |
| 150 | 12.98 | 3.63 | 67.02 | 16.37 |
| 300 | 2.60 | 0.62 | 80.77 | 16.01 |

When the % of remaining TZK was smaller than 3%, the reaction was stopped. The reaction solution contained TZA with a HPLC purity of 80.77%

EXAMPLE 11

Synthesis of 7-amino-3-[(1,2,5,6-tetrahydro-2-methyl-5,6-dioxo-1,2,4-triazin-3-yl)-thiomethyl]-cephalosporanic acid (TTA)

A filtrate (50 mL) from the strong anion exchanger Amberlite® (IRA-400 containing 0.0014 moles of 7β-(5-amino-5-carboxypentamido)-3-[(1,2,5,6-tetrahydro-2-methyl-5,6-dioxo-1,2,4-triazin-3-yl)-thiomethyl] cephalosporanic acid (hereinbelow indicated as TTC) with 92.2% purity (HPLC) and less than 0.2 mg/ml of 2,5-dihydro-3-mercapto-2-methyl-5,6-dioxo-1,2,4-triazine (TTZ) was adjusted to pH 6.75 with 3 M ammonia.

The TTC solution was fed into a 0.125 liter stirred glass vessel with 16 g of wet Eupergit C250L with a coimmobilized D-amino acid oxidase/catalase system (25 U of DAAO/g and 30 kU of catalase/g).

The conversion was performed at 20° C., 400 rpm and with an oxygen flow through a bottom diffuser of 0.1 vol/vol/min at 1 bar absolute pressure. The pH was titrated to pH 6.75 with 3 M ammonia by an autotitrator.

The conversion was controlled by HPLC in a reverse phase column Eclipse XDB-C8 150 mm×4.6 mm ID×5 µm; the mobile phase was 10 mM tetrabutylammonium hydrogen sulfate, 15 mM potassium dihydrogen phosphate, pH 6.5 containing 35% methanol at 1 ml/min with a 260 nm detection. The TTC appeared at 2.4 minutes, the TTK at 6.1 min and the TTG at 5.5 min, respectively.

Representative samples of the reaction mixture except for the enzyme were taken and the result obtained are reported as percentage of total β-lactams in the following table:

| Time (min) | % TTC | % TTK | % TTG | % Side products |
|---|---|---|---|---|
| 0 | 92.29 | 0.00 | 0.00 | 7.71 |
| 15 | 32.10 | 60.97 | 0.10 | 6.83 |
| 60 | 1.22 | 90.00 | 0.12 | 8.66 |

When the % of remaining TTC was smaller than 3%, the reaction was stopped and the reaction solution, containing TTK with a HPLC purity of 90.0%, was filtered off, and adjusted to pH 7.25 with 3 M ammonia.

The TTK solution was fed into a 0.125 liter stirred glass vessel with 23 g of wet Glutaryl-7-ACA Acylase (87 U/g). The conversion was performed at 20° C., 400 rpm at 1 bar absolute pressure. The pH was titrated to pH 7.25 with 3 M ammonia by an autotitrator.

The conversion was controlled by HPLC under the above-mentioned conditions. The TTA appeared at 2.9 min. Representative samples of the reaction mixture except for the enzyme were taken and the result obtained are reported as percentage of total β-lactams in the following table:

| Time (min) | % TTK | % TTG | % TTA | % Side products |
|---|---|---|---|---|
| 0 | 90.00 | 0.12 | 0.00 | 9.88 |
| 15 | 24.12 | 0.00 | 62.94 | 12.94 |
| 60 | 1.23 | 0.00 | 78.40 | 20.37 |

When the % of remaining TTK was smaller than 3%, the reaction was stopped. The reaction solution contained TTA with a HPLC purity of 78.40%.

EXAMPLE 12

Synthesis of 7-amino-3-[(5-methyl-1,3,4-thiadiazol-2-yl)-thiomethyl]-cephalosporanic acid (TDA) in a Single Step A filtrate (50 ml) from the strong anion exchanger Amberlite® (IRA400 containing 0.0011 moles of 7β-(5-amino-5-carboxypentamido)-3-[(5-methyl-1,3,4-thiadiazole-2-yl)-thiomethyl]cephalosporanic acid (hereinbelow indicated as TDC) with 95.41% purity (HPLC) and less than 0.2 mg/ml of 2-mercapto-5-methyl-1,3,4-thiadiazole (MMTD) was adjusted to pH 7.25 with 3 M ammonia.

The TDC solution was fed into a 0.125 liter stirred glass vessel with 16 g of wet Eupergit C250L with a co-immobilised D-amino acid oxidase/catalase system (25 U of DAAO/g and 30 kU of catalase/g) and 23 g of wet Glutaryl-7-ACA Acylase (87 U/g).

The conversion was performed at 20° C., 400 rpm and with an oxygen flow through a bottom diffuser of 0.1 vol/vol/min at 1 bar absolute pressure. The pH was titrated to pH 7.25 with 3 M ammonia by an autotitrator.

The conversion was controlled by HPLC in a reverse phase column Eclipse XDB-C8 150 mm×4.6 mm ID×5µ; the mobile phase was 10 mM tetrabutylammonium hydrogen sulfate, 15 mM potassium dihydrogen phosphate, pH 6.5 containing 35% methanol at 1 ml/min with a 260 nm detection. The TDC appeared at 3.0 min, the TDK at 10.9 min, the TDG at 8.1 min and the TDA at 4.1 min, respectively.

Representative samples of the reaction mixture except for the enzyme were taken and the result obtained are reported as percentage of total β-lactams in the following table:

| Time (min) | % TDC | % TDK | % TDG | % TDA | % Side Products |
|---|---|---|---|---|---|
| 0 | 95.42 | 0.00 | 0.00 | 0.00 | 4.58 |
| 15 | 28.50 | 27.11 | 3.43 | 36.51 | 4.45 |
| 60 | 13.27 | 11.87 | 0.00 | 70.17 | 4.69 |
| 150 | 0.00 | 0.00 | 0.00 | 95.13 | 4.87 |

When the % of remaining TDK was smaller than 3%, the reaction was stopped. The reaction solution contained TDA with a HPLC purity of 95.13%.

EXAMPLE 13

Synthesis of 7-amino-3-1(1-methyl-1H-tetrazol-5-yl)-thiomethyl]-cephalosporanic acid (TZA) in a Single Step A filtrate (50 ml) from the strong anion exchanger Amberlite® IRA-400 containing 0.00195 moles of 7β-(5-amino- 5-carboxypentamido)-3-[(1-methyl-1H-tetrazol-5-yl)-thiomethyl]cephalosporanic acid (hereinbelow indicated as TZC) with 93.55% purity (HPLC) and less than 0.2 mg/ml of 5-mercapto-1-methyltetrazole (MMRZ) was adjusted to pH 7.25 with 3 M ammonia.

The TZC solution was fed into a 0.125 liter stirred glass vessel with 16 g of wet Eupergit C250L with a co-immobilised D-amino acid oxidase/catalase system (25 U of DAAO/g and 30 kU of catalase/g) and 23 g of wet Glutaryl-7-ACA Acylase (87 U/g).

The conversion was performed at 20° C., 400 rpm and with an oxygen flow through a bottom diffuser of 0.1 vol/vol/min at 1 bar absolute pressure. The pH was titrated to pH 7.25 with 3 M ammonia by an autotitrator.

The conversion was controlled by HPLC in a reverse phase column Eclipse XDB-C8 150 mm×4.6 mm ID×5μ; the mobile phase was 10 mM tetrabutylammonium hydrogen sulfate, 15 mM potassium dihydrogen phosphate, pH 6.5 containing 35% methanol at 1 ml/min with a 260 nm detection. The TZC appeared at 2.1 minutes, the TZK at 5.0 min, the TZG at 4.3 min, and the TZA at 2.5 min, respectively.

Representative samples of the reaction mixture except for the enzyme were taken and the result obtained are reported as percentage of total β-lactams in the following table:

| Time (min) | % TZC | % TZK | % TZG | % TZA | % Side products |
|---|---|---|---|---|---|
| 0 | 93.55 | 0.00 | 0.00 | 0.00 | 6.45 |
| 30 | 11.46 | 53.00 | 4.78 | 19.39 | 11.37 |
| 90 | 0.00 | 40.20 | 7.32 | 36.56 | 15.92 |
| 180 | 0.00 | 25.69 | 5.75 | 50.43 | 18.13 |
| 370 | 0.00 | 2.84 | 0.42 | 78.17 | 18.57 |

When the % of remaining TZK was smaller than 3%, the reaction was stopped. The reaction solution contained TZA with a HPLC purity of 78.17%.

EXAMPLE 14

Synthesis of 7-amino-3-[(1,2,5,6-tetrahydro-2-methyl-5,6-dioxo-1,2,4-triazin-3-yl)-thiomethyl]-cephalosporanic acid (TTA) in a Single Step A filtrate (50 ml) from the strong anion exchanger Amberlite® IRA-400 containing 0.0016 moles of 7β-(5-amino-5-carboxypentamido)-3-[(1,2,5,6-tetrahydro-2-methyl-5,6-dioxo-1,2,4-triazin-3-yl)-thiomethyl]cephalosporanic acid (hereinbelow indicated as TTC) with 91.1% purity (HPLC) and less than 0.2 mg/ml of 2,5-dihydro-3-mercapto-2-methyl-5,6-dioxo-1,2,4-triazine (TTZ) was adjusted to pH 7.25 with 3 M ammonia.

The TTC solution was fed into a 0.125 liter stirred glass vessel with 16 g of wet Eupergit C250L with a co-immobilised D-amino acid oxidase/catalase system (25 U of DAAO/g and 30 kU of catalase/g) and 23 g of wet Glutaryl-7-ACA Acylase (87 U/g).

The conversion was performed at 20° C., 400 rpm and with an oxygen flow through a bottom diffuser of 0.1 vol/vol/min at 1 bar absolute pressure. The pH was titrated to pH 7.25 with 3 M ammonia by an autotitrator.

The conversion was controlled by HPLC in a reverse phase column Eclipse XDB-C8 150 mm×4.6 mm ID×5μ; the mobile phase was 10 mM tetrabutylammonium hydrogen sulfate, 15 mM potassium dihydrogen phosphate, pH 6.5 containing 35% methanol at 1 ml/min with a 260 nm detection. The TTC appeared at 2.4 minutes, the TTK at 6.1 min, the TTG at 5.5 min and the TTA at 2.9, respectively.

Representative samples of the reaction mixture except for the enzyme were taken and the result obtained are reported as percentage of total β-lactams in the following table:

| Time (min) | % TTC | % TTK | % TTG | % TTA | % Side products |
|---|---|---|---|---|---|
| 0 | 91.11 | 0.00 | 0.00 | 0.00 | 8.89 |
| 15 | 41.53 | 15.87 | 0.00 | 36.27 | 6.33 |
| 60 | 0.00 | 6.79 | 0.00 | 80.38 | 12.83 |
| 120 | 0.00 | 0.00 | 0.00 | 88.69 | 11.31 |

When the % of remaining TTK was smaller than 3%, the reaction was stopped. The reaction solution contained TTA with a HPLC purity of 88.69%

The invention is not limited to the embodiments hereinbefore described which may be varied in detail.

What is claimed is:

1. A process for preparing cephalosporanic acid derivatives comprising the steps of:

enzymatically converting a 3-thiolated cephalosporin C compound of formula III:

(III)

3-thiolated cephalosporin C (T'X'C)

into a 3-thiolated-α-ketoadipyl-7-aminocephalosporanic acid derivative of formula IV:

(IV)

wherein R is a heterocyclic group comprising at least a nitrogen atom.

2. The process as claimed in claim 1 wherein the compound of formula III is enzymatically converted into a compound of formula IV by an immobilised enzyme system.

3. The process as claimed in claim 2 wherein the enzyme system comprises co-immobilised D-Amino acid oxidase and catalase.

4. The process as claimed in claim 3 wherein the enzymatic conversion is carried out in the presence of molecular oxygen, at a pressure of 1 to 5 bar absolute, a pH of from 6.5 to 8.0 and at a temperature of from 15 to 30° C. for a period of from 30 mins to 180 mins.

5. The process as claimed in claim 1 comprising the step of separating the enzyme system from the reaction mixture.

6. The process as claimed in claim 1 including the step of purifying the compound of formula IV.

7. The process as claimed in claim 6 wherein the compound is purified using an adsorption column.

8. The process as claimed in claim 1 wherein the enzymes are co-immobilised using a suitable cross-linker agent in a suitable solid support.

9. The process as claimed in claim 8 wherein the enzymes are in the form of crystals of a size suitable for use as a biocatalyst.

10. The process as claimed in claim 1 wherein the enzymatic processes are carried out while maintaining the enzyme in dispersion in an aqueous substrate solution.

11. The process as claimed in claim 1 wherein the enzymatic process is carried out in a column.

12. The process as claimed in claim 1 including the step of recovering the enzyme for reuse.

13. The process as claimed in claim 5, wherein the step of separating the enzyme system from the reaction mixture is performed by filtration.

14. The process as claimed in claim 1 wherein R is a heterocyclic group comprising at least one nitrogen atom and optionally a sulphur or oxygen atom.

15. The process as claimed in claim 14 wherein R is a heterocyclic group selected from any one or more of the group comprising thienyl, diazolyl, tetrazolyl, thiazolyl, triazinyl, oxazolyl, oxadiazolyl, pyridyl, pirimidinyl, benzothiazolyl, benzimidazolyl, benzoxazolyl, or any derivative thereof, preferably 5-methyl-1,3,4-thiadiazol-2-yl, 1-methyl-1H-tetrazol-5-yl or 1,2,5,6-tetrahydro-2-methyl-5,6-dioxo-1,2,4-triazin-3-yl.

* * * * *